Figure 1:
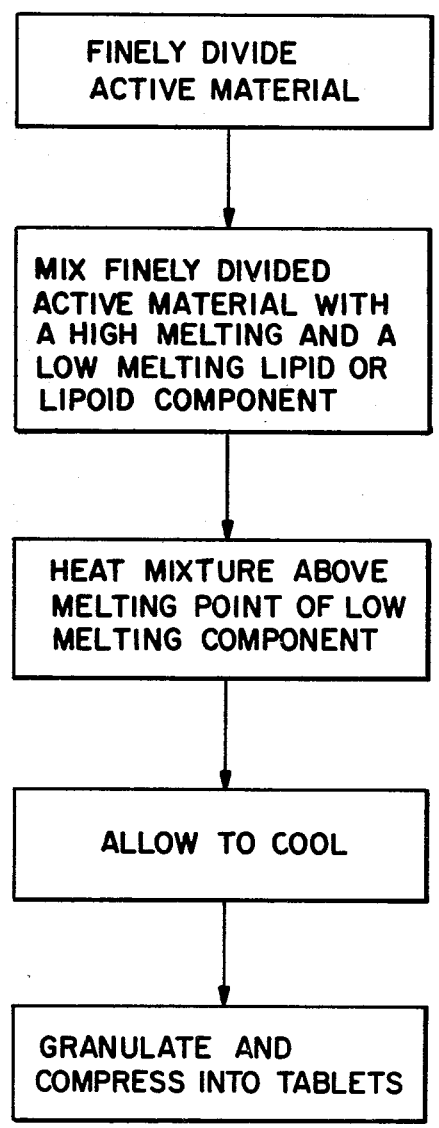

United States Patent [19]

Augart

[11] Patent Number: 4,483,847

[45] Date of Patent: Nov. 20, 1984

[54] PROCESS FOR THE MANUFACTURE OF A PHARMACEUTICAL COMPOSITION WITH A RETARDED LIBERATION OF ACTIVE MATERIAL

[75] Inventor: Helmut Augart, Waldkirch, Fed. Rep. of Germany

[73] Assignee: Warner-Lambert Company, Morris Plains, N.J.

[21] Appl. No.: 534,020

[22] Filed: Sep. 20, 1983

Related U.S. Application Data

[63] Continuation of Ser. No. 358,746, Mar. 16, 1982, , which is a continuation of Ser. No. 277,559, Jun. 26, 1981, abandoned.

[30] Foreign Application Priority Data

Jun. 28, 1980 [DE] Fed. Rep. of Germany ..... 30244167

[51] Int. Cl.$^3$ .......................... A61K 9/26; A61K 9/42
[52] U.S. Cl. ....................................... 424/22; 424/19; 424/38
[58] Field of Search .................................. 424/19–22, 424/38

[56] References Cited

U.S. PATENT DOCUMENTS

| | | | |
|---|---|---|---|
| 2,875,130 | 2/1959 | Grass et al. | 424/22 |
| 3,108,046 | 10/1963 | Harbit et al. | 424/22 |
| 3,146,167 | 8/1964 | Lantz et al. | 424/22 |
| 3,184,386 | 5/1965 | Stephenson | 424/22 |
| 3,279,998 | 10/1966 | Raff et al. | 424/22 |
| 3,308,217 | 3/1967 | Lowy et al. | 424/22 |
| 3,374,146 | 3/1968 | Blicharz et al. | 424/22 |
| 3,670,065 | 6/1972 | Erickson et al. | 424/22 |
| 4,132,753 | 1/1979 | Bilchare et al. | 424/22 |

FOREIGN PATENT DOCUMENTS 0829450 9/1975 Belgium .
2033911 2/1972 Fed. Rep. of Germany .

*Primary Examiner*—Shep K. Rose
*Attorney, Agent, or Firm*—Ronald A. Daignault

[57] ABSTRACT

The present invention provides a process for the production of a pharmaceutical composition with a retarded liberation of active material, wherein an active material in finely divided form is mixed with a finely divided high melting and a low melting lipid or lipoid component, the mixture is brought to a temperature which is above the melting point of the low melting component but below the melting point of the high melting component and the mixture, after melting of the low melting component, is allowed to cool to below the melting point thereof and subsequently worked up in known manner to give a finished pharmaceutical composition.

9 Claims, 1 Drawing Figure

PROCESS FOR MANUFACTURE OF A PHARMACEUTICAL COMPOSITION WITH A RETARDED LIBERATION OF ACTIVE MATERIAL

PROCESS FOR THE MANUFACTURE OF A PHARMACEUTICAL COMPOSITION WITH A RETARDED LIBERATION OF ACTIVE MATERIAL

This application is a continuation of copending U.S. Ser. No. 358,746, filed Mar. 16, 1982 which is a continuation of U.S. Ser. No. 277,559, filed June 26, 1981, now abandoned.

The present invention is concerned with a process for the production of pharmaceutical compositions with a retarded liberation of active material, such compositions being known as retard compositions.

A number of processes are known for the production of pharmaceutical compositions in retard form. Many of them suffer from the substantial disadvantage that organic solvents are needed for their production, whereas others require the use of expensive or physiologically undesirable adjuvants.

In order to avoid these disadvantages, attempts have been made to use lipid materials for the production of retard compositions by embedding particles of active materials in lipid materials. A large number of such lipid materials are available and many processes have been described for the production of retard forms using lipid materials. Normally, certain swelling agents or disintegrating agents are added to the formulations in order to prevent compressed forms made from active materials embedded in such lipid materials liberating the active materials too slowly or in order to prevent the danger that some of the so formulated active material is not liberated at all during passage through the body and can thus be resorbed. Thus, these lipid materials perform a control function.

In the case of the production of retard forms in which the embedding of the active material in the lipid material represents the actual retard principle, the lipid materials normally employed have a melting point which, as a rule, is in the range of from 80° to 90° C. In this case, it is preferable to melt the lipid material or mixture of lipid materials and slowly to introduce the active materials or possibly mixtures thereof with adjuvant materials into the melt, taking care that there is no localised cooling since otherwise disturbing inhomogeneities will arise.

It is advantageous when lipid materials are used which are available in powdered form since previously prepared homogeneous mixtures of active materials and lipid materials can be heated above the melting temperature of the lipid materials, whereby embedding takes place. These masses can be converted into a granulate form by granulation during the cooling or by grinding after the cooling.

This process is admittedly economical insofar as it avoids the use of organic solvents. However, it does involve very considerable disadvantages. The use of steam-heated kettles and hot melts involves a danger of accidents and only very temperature-stable active materials can be worked up at the relatively high melting temperatures involved.

In order to avoid high melting temperatures, retard tablets have also been produced on the basis of lipids by mixing lipid materials with melting points of preferably from 55° to 88° C. with active materials at ambient temperature and then pressing the mixture obtained into tablets (see Federal Republic of Germany Patent Specification No. 1,492,123). However, this process is also unsatisfactory because the pharmaceutical compositions thus produced always have a certain porosity which cannot be eliminated by increasing the amount of pressure applied. This results in undesirable inhomogeneities and a rapid disintegration which can scarcely be controlled.

A further solution to the problem was sought by mixing particles of pharmaceutical materials with a wax additive material which is solid at ambient temperature but melts at a temperature at which the pharmaceutical material is not disadvantageously affected, followed by pressing this mixture to form tablet cores and providing the tablet cores with a coating which keeps its shape at a temperature at which the wax additive material melts (see Federal Republic of Germany Patent Specification No. 1,617,657). The coated cores thus produced were then heated to above the melting point of the wax additive material and, after cooling, were ready for use. This very laborious depot process has, in turn, the disadvantage that it is only possible to use active materials which are stable at the high temperatures used for melting the wax additive material in the coated cores.

Surprisingly, we have now found that for embedding an active material by melting a lipid or lipoid component, it is not necessary entirely to heat this component to a high temperature but that complete embedding can be achieved at considerably lower temperatures when the active material to be retarded is mixed with a high melting and a low melting lipid or lipoid component and the mixture is only heated to above the melting temperature of the low melting component.

Thus, according to the present invention, there is provided a process for the production of a pharmaceutical composition with a retarded liberation of active material, wherein an active material in finely divided form is mixed with a finely divided high melting and a low melting lipid or lipoid component, the mixture is brought to a temperature which is above the melting point of the low melting component but below the melting point of the high melting component and the mixture, after melting of the low melting component, is allowed to cool to below melting point thereof and subsequently worked up in known manner to give a finished pharmaceutical composition FIG. 1 illustrates the process of the present process.

The lipid or lipoid components used can be conventional water-insoluble support materials, for example fatty alcohols and especially higher alkanols containing more than 13 and especially 16 to 20 carbon atoms, such as cetyl and stearyl alcohol, as well as mixtures thereof. Use can also be made of fatty acids which bring about a liberation of the active material dependent upon the pH, especially higher alkane-carboxylic acids, for example stearic acid. Glycerides, especially hydrogenated vegetable oils, such as hydrogenated cottonseed oil or castor oil, as well as mono-, di- and triesters of glycerol with palmitic acid or stearic acid or mixtures thereof can also be used. Furthermore, pulverised, wax-like materials of vegetable, animal, mineral or synthetic origin can be used. The lipophilic salts of fatty acids, such as magnesium stearate are also very suitable. It is only necessary that the retarding material is stable in the intended temperature range and is physiologically inert and also that it does not react with the pharmaceutically active material.

The high melting component preferably has a melting point above 70° C., there being no upper limit because this component, according to the present invention, does not have to be melted. However, a temperature range of from 80° to 100° C. is preferred.

The low melting component should have a melting point below that of the high melting component, i.e. it should melt below 70° C. The lower limit is determined by the lowest temperature at which the mixture can be worked up. Thus, below 30° C., the mixture begins to become increasingly smeary so that, for normal use, the lower limit should be about 30° C. However, in practice, the preferred range is 50° to 60° C.

The weight ratio of the two components can be varied within very wide limits. In practice, weight ratios of 1:9 to 9:1 are completely acceptable. However, in most cases, use is made of mixtures with a weight ratio of 1:5 to 5:1 and preferably of 1:3 to 3:1. The determination of the most favourable weight ratio can be carried out empirically, without difficulty, for every mixture.

The important parameters are the particle size and the amount of the active and additional materials. Thus, the liquid, low melting lipid or lipoid component can be regarded as filling the hollow spaces which are formed by the adjacent particles of the high melting component and of the adjuvant and active materials, a product being obtained in which the particles of the higher melting component and those of the adjuvant and additional materials can be regarded as being embedded like gravel in concrete in which the solidified melt of the lower melting component is like the cement.

According to the process of the present invention, a product is, surprisingly, obtained, the pharmaceutical quality of which does not differ from that of the previously known products manufactured by melting at much higher temperatures. The pharmaceutical formulations are characterised by a uniform liberation of the active material over a long period of time. In particular, the liberation can be outstandingly well controlled by means of embedding in the mentioned lipid or lipoid components.

However, the process according to the present invention has considerable advantages in comparison with the prior art:
1. the active materials can be worked up much more gently at the low temperature;
2. due to the low working temperature used, the danger of accidents is practically completely excluded;
3. the partial melting at a low temperature results in a considerable saving of energy;
4. the apparatus used can be of substantially simpler construction (instead of steam-heated, double-walled mixers, it is possible to employ simple vessels operated with the use of hot water) and if friction mixers and extruders are used, additional heating can be completely omitted.

The process can be carried out in the following manner: a powdered mixture is first prepared of the active material or materials, of the lipid or lipoid components, as well as of conventional filling materials and disintegrating materials or swelling agents as liberation controlling components.

After homogeneous mixing, the mixture obtained is heated, while stirring, until the low melting component melts and the mass starts to sinter. After complete melting of the low melting component, air is forced out, possibly with the application of mechanical pressure, so that, after cooling, a practically pore-free sintered mass is obtained.

Examples of filling materials which can be used include lactose, saccharose and calcium phosphate. Disintegrating agents or swelling agents which serve to control the liberation of the active materials are, for example, water-soluble or water-swellable materials, such as methyl cellulose, various synthetic polymers, natural materials, for example guar gum, and, preferably, carboxymethylcelluloses.

The apparatus used can be, for example, a low speed mixing kneader or a high speed rapid mixer with mixing propellers.

The above-described melt granulates can also be produced in fluidised bed granulators or in fluidised bed driers since the necessary temperatures can easily be achieved in such apparatus. Friction mixers are also suitable since, in that case, if desired, heating does not have to be carried out because the powder mixtures heat up sufficiently in a few minutes at 1000 to 1500 r.p.m. Finally, cogwheel granulating machines can also be used since they permit a continuous operation with a very high throughput capacity. The powder mixtures can even be extruded non-porously at temperatures of about 50° C. with little pressure.

After melting and before cooling, the mass is preferably additionally positively compressed by means of appropriate mechanical devices, for example extruders or friction mixers.

After this compressing, the mass can be granulated in any appropriate manner during cooling or can be granulated after cooling is complete. If desired, lubricants can be added to the granulate. The granulate can be pressed to give tablets, the active material liberation of which can be adjusted by appropriate formulation of the composition. If desired, such pressed bodies can also be drageed or film coated. Furthermore, the granulates can also be worked up to give multi-layer tablets in that, for example, they are worked up to give a two-layer tablet with a second layer which contains a nonretarded initial dose. The granulates can also be filled into hard gelatine capsules, if desired after further coating the granulate particles. Finally, it is also possible to work up several different retard granulates together to give, for example, a tablet.

The following comparative experiments show that the pharmaceutical compositions produced by the process according to the present invention do not differ practically from conventional pharmaceutical compositions with regard to their disintegration time. For this purpose, the following active material-free powder mixture was prepared:

| | |
|---|---|
| lactose | 7500 g. |
| finely powdered hydrogenated castor oil (high melting component - m.p. about 85° C.) | 500 g. |
| finely powdered stearic acid (low melting component - m.p about 55° C.) | 2000 g. |
| pulverised carboxymethyl-cellulose | 100 g. |

The powder mixture was worked up in various ways to give tablets, the disintegration times of which were then determined in simulated digestive juice according to the procedure given in NF XIV:

I. Conventional production (melt at 100° C.)

The powder mixture was heated in a low speed mixing kneader at 100° C., kneaded for 15 minutes and the mass, after cooling to ambient temperature, ground to give a granulate. Tablets with a definite specification were pressed therefrom (tablet diameter 11 mm., thickness 5.2 mm., breaking strength 90N).

II. Process according to the present invention (melt at 60° C.)

(A) The powder mixture was heated to 60° C. according to the process of the present invention in a high-speed rapid mixer, compressed for 5 minutes and, after cooling to ambient temperature, ground to give a granulate. Tablets were pressed therefrom with the specification given in I.

(B) The powder mixture was introduced into a cogwheel granulating machine, the rollers of which had been heated to about 40° C. with warm water. The mass was extruded through the bores under the roller pressure at a temperature of 54° C. The sieve granulate thus obtained was ground to give a granulate from which tablets were pressed with the specification given in I.

(C) The powder mixture was heated to 60° C. in a low speed planet mixing kneader, kneaded for 15 minutes and the mass, after cooling to ambient temperature, ground to give a granulate from which tablets were pressed with the specification given in I.

(D) The powder mixture was heated in a fluidised bed granulator, with occasional shaking, with an air supply at 85° C., the product temperature being 60° C. After cooling, the mass was ground and pressed to give tablets with the specification given in I.

(E) The powder mixture was moved about in a friction mixer at about 1300 r.p.m. until it had melted. Melting of the low melting component took place at about 60° C. after about 4 minutes. The mass was removed from the mixer and, after cooling to ambient temperature, ground to give a granulate from which tablets were pressed with the specification given in I.

III. Pressing process without melting.

(A) The powder mixture was heated in a high speed rapid mixture to 50° C., i.e. below the melting point of the lower melting component, consolidated for 5 minutes and, after cooling to ambient temperature, ground to give a granulate from which tablets were pressed with the specification given in I.

(B) The powder mixture was pressed, without heating, with conventional pressure to give tablets with the specification given in I. The breaking strength of the tablets was 72N.

(C) The powder mixture was pressed, without heating, under the highest possible pressing force as in (B) to give tablets with a breaking strength of 88N. Because of the high pressing force used, the thickness of the tablets was 4.8 mm.

The following Table shows what percentage of the compositions had disintegrated after a given disintegration time:

TABLE

| disintegration time | 1 h. | 2 h. | 3.5 h. | 5 h. | 7 h. |
| --- | --- | --- | --- | --- | --- |
| I | 22 | 30 | 45 | 80 | 95 |
| II A | 22 | 33 | 48 | 74 | 94 |
| II B | 23 | 39 | 60 | 91 | 97 |
| II C | 21 | 29 | 43 | 72 | 96 |
| II D | 31 | 48 | 65 | 83 | 97 |
| II E | 21 | 32 | 44 | 69 | 93 |
| III A | 42 | 62 | 75 | 90 | 96 |
| III B | 82 | 84 | 85 | 88 | 99 |
| III C | 83 | 85 | 86 | 88 | 99 |

It can be seen from the above Table that the composition described under I completely correspond in their disintegration time with the products described under II. However, the products described under III show that, by means of simple pressing, even under the highest possible pressure, a useful retarding cannot be achieved. After at most 2 hours, the compositions have substantially completely disintegrated.

The following Examples are given for the purpose of illustrating the present invention:

EXAMPLE 1

Film tablets containing 45 mg. norfenefrine

Composition:

| | |
| --- | --- |
| lactose PhEur. | 2700 g. |
| norfenefrine hydrochloride | 1000 g. |
| carboxymethylcellulose | 50 g. |
| hydrogenated castor oil | 250 g. |
| stearic acid | 1000 g. |

For the production of the retard tablets, all the above-mentioned materials are placed in a rapid mixer with a double wall and homogeneously mixed. The double wall is heated until the mixture has reached a temperature of 60° C. The mass thereby solidifies and is removed and cooled to ambient temperature. The cooled mass is ground to give a granulate from which tablets are pressed with a diameter of 9 mm. and a weight of 225 mg., these tablets then being provided with a film coating.

EXAMPLE 2

Tablets containing 15 mg. norfenefrine hydrochloride

Composition:

| | |
| --- | --- |
| lactose PhEur. | 2700 g. |
| norfenefrine hydrochloride | 1000 g. |
| carboxymethylcellulose | 50 g. |
| hydrogenated castor oil | 1583 g. |
| stearic acid | 1000 g. |

A granulate is produced from the components in the manner described in Example 1 from which are pressed tablets with a weight of 95 mg. and a diameter of 6 mm.

EXAMPLE 3

Tablets containing 80 mg. pentaerythrityl tetranitrate

Composition:

| | |
| --- | --- |
| pentaerythrityl tetranitrate (16%) | 3200 g. |
| lactose | 500 g. |
| carboxymethylcellulose | 50 g. |
| hydrogenated castor oil | 250 g. |
| stearic acid | 1000 g. |

For the production of retard tablets, the powdered raw materials are introduced into a planet mixer with a double wall and homogeneously mixed and heated until the powder mixture has reached a temperature of 60° C. and has thereby solidified. The mass is removed from the mixer while still warm and, after cooling, ground to give a granulate from which are produced tablets with a weight of 750 mg. and a diameter of 11 mm.

EXAMPLE 4

Tablets containing 45 mg NORFENEFRIN HCl

| | |
|---|---|
| Lactose, Ph. Eur. | 2430 g |
| Norfenefrin HCl | 900 g |
| Carboxymethylcellulose | 45 g |
| Magnesium stearate | 450 g |
| Stearic acid | 675 g |

For the manufacture of sustained-release tablets all the substances are mixed homogenously in a planetary mixer with a double lining. The double lining is heated until the mixture reaches a temperature of 60° C. After setting the mass is removed, cooled and ground into a granular form. The granules are pressed into tablets with a diameter of 9 mm and a weight of 225 mg.

EXAMPLE 5

Tablets containing 40 mg ISOSORBIDE DINITRATE

| | |
|---|---|
| Isosorbide dinitrate, ground in lactose (25%) | 240 g |
| Lactose, Ph. Eur. | 145 g |
| Carboxymethylcellulose | 5 g |
| Hydrated castor-oil | 25 g |
| Stearic acid | 100 g |

The powders are mixed homogenously and the mixture heated to 60° C. in a boiler with a double lining. The warm mass is forced through a wide-mesh sieve. After cooling the mass is ground into tablet granules and pressed into oval-shaped tablets weighing 343.3 mg.

EXAMPLE 6

Tablets containing 30 mg VINCAMIN

| | |
|---|---|
| Vincamin HCl | 73.33 g |
| Lactose, Ph. Eur. | 296.67 g |
| Carboxylmethylcellulose | 5 g |
| Hydrated castor-oil | 25 g |
| Stearic acid | 100 g |

All the raw materials are thoroughly mixed and heated to 60° C. in a water bath. The warm mass is passed through a granulating machine. After cooling the mass is ground into tablet granules, which are then pressed into tablets with a diameter of 9 mm and a weight of 225 mg.

I claim:

1. An improved process for the production of a pharmaceutical composition with a retarded liberation of active material, including active material which is unstable above 70° C., wherein the improvement comprises
   (a) mixing said active material and finely divided particle form with finely divided particles of high melting and a low melting lipid or lipoid component, in a weight ratio of 1:9 to 1 wherein the melting point of the high melting component is above 70° C. and the melting point of the low melting component is from about 30° C. to below about 70° C. wherein the lipid or lipoid component is a fatty alcohol, containing 13-20 carbon atoms or a mixture thereof, a fatty acid, a lipophilic stearate, a hydrogenated vegetable oil or mono-, di- and triester of glycerol with palmitic acid or stearic acid or mixtures thereof or a vegetable, animal, mineral or synthetic wax.
   (b) bringing the mixture to a temperature which is above the melting point of the low melting component but below the melting point of the high melting component thereby embedding particles of the high melting component and active material in the low melting component like gravel in concrete in cement and
   (c) after melting of the low melting component, allowing the mixture to cool below the melting point thereof.

2. A process according to claim 1, wherein the melting point of the low melting component is below 70° C.

3. A process according to claim 2, wherein the melting point of the low melting component is in the range of from 50° to 60° C.

4. A process according to claim 1, wherein the melting point of the high melting component is above 70° C.

5. A process according to claim 4, wherein the melting point of the high melting component is in the range of from 80° to 100° C.

6. A process according to claim 1, wherein the two components are used in a weight ratio of from 1:9 to 9:1.

7. A process according to claim 6, wherein the weight ratio of the two components is 1:5 to 5:1.

8. A process according to claim 7, wherein the weight ratio of the two components is 1:3 to 3:1.

9. A process according to claim 1, wherein the lipid or lipoid component is a fatty alcohol, a fatty acid, a lipophilic salt of a fatty acid, a glyceride or a wax-like material of vegetable, animal, mineral or synthetic origin.

* * * * *